United States Patent [19]

Miserlis

[11] 4,435,580

[45] Mar. 6, 1984

[54] PROCESS FOR THE PRODUCTION OF PHTHALIC ANHYDRIDE

[75] Inventor: Constantine D. Miserlis, Arlington, Mass.

[73] Assignee: The Badger Company, Inc., Cambridge, Mass.

[21] Appl. No.: 374,284

[22] Filed: May 3, 1982

[51] Int. Cl.³ ............................................. C07D 307/89
[52] U.S. Cl. .................................... 549/248; 549/249; 549/250; 549/256; 549/257; 549/258
[58] Field of Search ............... 549/248, 249, 250, 256, 549/257, 258

[56] References Cited

U.S. PATENT DOCUMENTS 4,215,053  7/1980  Palmer ................................. 549/248

Primary Examiner—Richard Raymond
Attorney, Agent, or Firm—Schiller & Pandiscio

[57] ABSTRACT

A system for producing phthalic anhydride by the catalytic oxidation of naphthalene, wherein without creating a significant pressure drop in the system substantially all of the catalyst particles are removed from the product stream before the product stream is sent to a battery of switch condensers for recovery of the phthalic anhydride.

20 Claims, 2 Drawing Figures

PROCESS FOR THE PRODUCTION OF PHTHALIC ANHYDRIDE

FIELD OF THE INVENTION

This invention relates to the production of acid anhydrides in general, and more particularly to the production of acid anhydrides by catalytic oxidation of aromatic hydrocarbons, e.g., production of phthalic anhydride by oxidation of napthalene.

BACKGROUND OF THE INVENTION

It is well known in the art that anhydrides of carboxylic and dicarboxylic acids may be produced by catalytic oxidation of aromatic hydrocarbons such as benzene, o-xylene, naphthalene, or of unsaturated aliphatic hydrocarbons such as butadiene, n-butene, and mixtures thereof. In general, phthalic anhydride production is achieved by reacting naphthalene or o-xylene vapors with an oxygen-bearing gas in a reactor, under appropriate temperature and pressure conditions and in the presence of a suitable catalyst, e.g., a vanadium pentoxide-bearing catalyst. The phthalic anhydride produced by the reaction is contained in the reactor effluent and is subsequently separated out and recovered.

FIG. 1 shows in more detail a conventional system for the production of phthalic anhydride by catalytic oxidation of naphthalene. Oxygen-bearing air is compressed by a compressor 2 driven by a motor 3 and is sent to an air receiver 4. A stream of air from air receiver 4 is heated to about 300° F. in an air heater 6 and then enters the bottom of a fluidized catalytic reactor 8. This air passes through a grid 10 into a vanadium pentoxide-bearing catalyst bed 12 which is disposed on grid 10. The air entering the bottom end of the reactor is pressurized to about 37 psig.

Molten naphthalene is pumped from a storage tank 14 by a metering pump 16 through a vaporizer 18 where the naphthalene is vaporized before being injected into catalyst bed 12. Bed 12 is fluidized by the air and the primary oxygen/naphthalene reaction takes place in contact with catalyst bed 12. The rate at which the molten naphthalene is introduced into bed 12 is coordinated with the rate at which the oxygen-bearing air is introduced into bed 12 so that the reactor's catalyst bed 12 receives air and naphthalene in a ratio of about 10:1 by weight. Bed 12 is maintained at a reaction temperature of between about 600° and about 750° F. by means of suitable temperature control elements 20.

Reacted gases flow upward out of the top of fluidized catalyst bed 12 to a catalyst disengagement zone 22 where any catalyst particles which may have been carried upward from bed 12 by the rising gases disengage from the gases and settle back down onto bed 12. The reacted gases continue to rise and pass through a grid 24 and into a vanadium pentoxide-bearing catalyst bed 26 which resides on grid 24. Bed 26 is in turn fluidized by these gases. Catalyst bed 26 serves as a quench bed for the reacted gases, and to this end bed 26 is maintained at the appropriate quench temperature of about 525° F. by means of temperature control elements 28. The latter, like temperature control elements 20, may be individually controlled U-shaped tubular heat exchangers carrying a suitable heat exchange fluid. The quenched gases thereafter pass from fluidized catalyst bed 26 to a disengagement zone 30 where catalyst particles which may have been carried from bed 26 by the rising gases will tend to disengage from the gases and settle back down onto bed 26.

A plurality of cyclones 32 are positioned at the top end of disengagement zone 30 and are intended to purge the reacted gases of any lingering catalyst particles before the gaseous effluent leaves the reactor and is processed to recover desired components. Each cyclone is provided with a dip-leg 34 for returning the separated catalyst fines back to catalyst beds 12 and 26.

The gas stream leaving cyclones 32 is passed through a gas cooler 36 where the stream is cooled to a temperature just above the dew point of phthalic anhydride, i.e. approximately 315° F. The cooled stream then passes into a partial condenser 38 where up to approximately one-half of the phthalic anhydride that is present in the gaseous stream is condensed out as a liquid. The liquid phthalic anhydride is separated from the remaining gas stream and it flows via a line 39 to a liquid storage tank 40 for subsequent processing.

The gas stream exiting partial condenser 38 has a temperature of approximately 300° F. It passes via a line 41 and a pressure control valve 42 to one of a battery of switch condensers 44a, 44b, 44c, etc. Switch condensers 44a, 44b, 44c, etc. are intended to remove the phthalic anhydride remaining in the effluent stream by sublimating the phthalic anhydride out of the reactor effluent as a solid. When a given switch condenser has condensed out a predetermined amount of phthalic anhydride, the switch condenser is shut off from the incoming gas stream and is switched over to a heating cycle to melt the condensed phthalic anhydride. Simultaneously, another switch condenser, which at this point has been re-cooled after completing its heating cycle, is opened to the gas stream to sublimate incoming phthalic anhydride. The phthalic anhydride which is melted in any of the switch condensers flows to a liquid storage tank 46 for further processing. The effluent stream that leaves a cooling switch condenser is sent to a gas scrubber 48 where it is washed with water before being vented to the atmosphere or to other process equipment for further treatment or recovery. The gas stream preferably leaves the switch condensers at a temperature of between about 125° and about 140° F. before being directed to the scrubber 48.

Pressure control valve 42, disposed in the gas line intermediate partial condenser 38 and switch condensers 44a, 44b, 44c, etc., imposes the back pressure on reactor 8 which is necessary in the practice of this invention. Also, by controlling the gas pressure at this point in the process the phthalic anhydride can be condensed in partial condenser 38 as a liquid instead of as a solid. This is so, because increased pressure can raise the dew point of phthalic anhydride above the melting point, thereby permitting condensation of the phthalic anhydride directly as a liquid. In the system described above, the pressure control valve is designed to hold the reactor top pressure at about 22 psig.

Unfortunately, a number of difficulties arise when a production process of the sort just described is utilized. In particular, it has been found that the cyclones 32 are incapable of removing all of the catalyst dust from the reaction gases before the gases leave the reactor. As a result, small amounts of catalyst dust (typically between about 0.007% and about 1.0% by weight) leave the reactor with the effluent and travel on to the downstream process elements. The dust in the gaseous effluent passes through gas cooler 36, partial condenser 38 and pressure control valve 42 and enters switch condensers 44a, 44b, 44c, etc. Inside the switch condensers, the catalyst dust in the reactor effluent creates complications when the condensers switch to their cooling cycle to sublimate out phthalic anhydride from the gas as a solid. In particular, the dust particles serve as a nucleus for condensing phthalic anhydride and allow some of the phthalic anhydride in the effluent to condense out of the effluent as a gas-born mist rather than sublimating substantially entirely as a solid deposited directly on the surfaces of the switch condensers. This is a problem since the gas-born mist tends to deposit and solidify on the switch condenser surfaces as a dense, slushy mass which is relatively unporous and which has a relatively poor heat transfer coefficient, whereas sublimated phthalic anhydride deposits on the switch condenser surfaces as a group of needle-like crystals which are relatively porous and which have a relatively good heat transfer coefficient.

The relatively low porosity of the dense, slushy phthalic anhydride deposition (vis-a-vis the relatively high porosity of the sublimation deposited solid phthalic anhydride) is of concern since it tends to increase the back pressure within the switch condensers. Such an increase in back pressure within the switch condensers is undesirable since it reduces the efficiency of the system and necessitates the use of a bigger and more expensive compressor 2 (and hence a bigger and more expensive motor 3) in order to make the system function where significant amounts of slushy phthalic anhydride deposition ocurs. In this regard it is to be appreciated that the principal power requirement of a phthalic anhydride production system of the sort shown in FIG. 1 is the power requirement of the motor 3. Thus, the capital costs and operational costs of a phthalic anhydride production system tend to increase where significant amounts of the relatively unporous slushy phthalic anhydride deposition occurs.

In addition, the relatively poor heat transfer coefficient of the slushy phthalic anhydride deposition (vis-a-vis the relatively good heat transfer coefficient of the sublimated porous solid phthalic anhydride) is of concern since it can (a) increase the amount of time necessary for cooling the effluent stream to the temperature required to solidify the phthalic anhydride, and (b) increase the amount of time necessary for melting out deposited phthalic anhydride from a full switch condenser. In addition, the relatively poor heat transfer coefficient of the slushy phthalic anhydride deposits can cause the heat exchangers to perform more work to recover the same amount of phthalic anhydride. As a result, production times and costs tend to be higher where significant amounts of slushy phthalic anhydride deposition occurs.

Since such dust-related complications threaten the economic viability of a plant using the aforementioned phthalic anhydride production system, many attempts have been made to eliminate the catalyst dust from the effluent prior to the effluent's receipt by the switch condensers.

One way of reducing the amount of catalyst dust carried into the switch condensers in the effluent stream is to replace the cyclones 32 with a more effective type of filtration system, i.e. screens, micro-metallic filters, or fiber filters. Such filtration devices can be more effective than cyclones in reducing the amount of catalyst dust in the reactor effluent, but they tend to create a more severe pressure drop in the system. Since such an increase in the system's back pressure tends to drive up the system's capital investment and power costs for the reasons specified above, such a solution is not entirely satisfactory.

Attempts have also been made to reduce the amount of catalyst dust reaching the switch condensers by inserting a liquid entrainment separator between liquid condenser 38 and the battery of switch condensers 44. Such a construction allows the removal of any dust-based mist at the entrainment separator. However, it has been found that such a solution is not entirely satisfactory since some catalyst dust still gets by the entrainment separator and is available to combine with liquid phthalic anhydride in the switch condensers so as to cause the undesired slushy phthalic anhydride deposition.

OBJECTS OF THE PRESENT INVENTION

As a result, the principle object of the present invention is to provide a modified phthalic anhydride production system wherein the system is similar to the one shown in FIG. 1, yet is capable of removing substantially all the catalyst particles from the reactor effluent before the effluent reaches the switch condensers without causing a substantial pressure drop across the system.

SUMMARY OF THE INVENTION

These and other objects of the present invention are achieved by providing a production system substantially the same as the one shown in FIG. 1, except that a venturi scrubber stage is inserted into the system between the partial condenser 38 and pressure control valve 42. The venturi scrubber stage serves to remove, without imposing a substantial pressure drop, substantially all the catalyst dust contained in the reactor effluent so that the effluent may enter the switch condensers substantially free of catalyst dust. As a result, the phthalic anhydride condensed out in the switch condensers tends to be deposited via sublimation directly to a solid form that is relatively porous and has a good heat transfer coefficient, instead of as a dense, slushy phthalic anhydride deposition which is relatively unporous and which has a relatively poor heat transfer coefficient.

BRIEF DESCRIPTION OF THE DRAWINGS

Still other objects and features of the present invention will be more fully described or rendered obvious in the following detailed description of the preferred embodiment, which is to be considered together with the accompanying drawings wherein.

DETAILED DESCRIPTION OF THE PREFERRED EMBODIMENT

Figure 1:
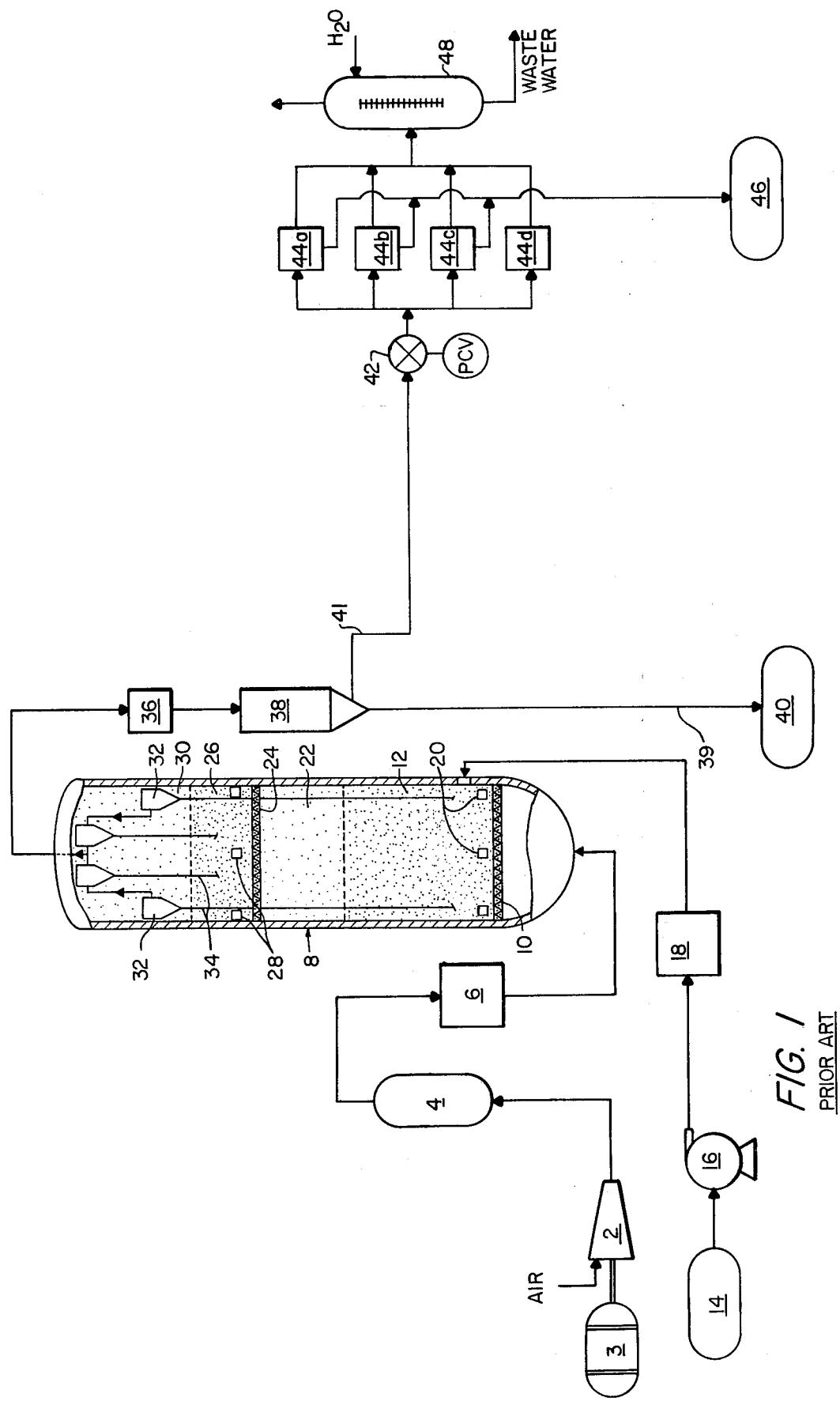
FIG. 1 is a process flow sheet showing a widely used prior art system for producing phthalic anhydride from catalytic oxidation of naphthalene.
Figure 2:
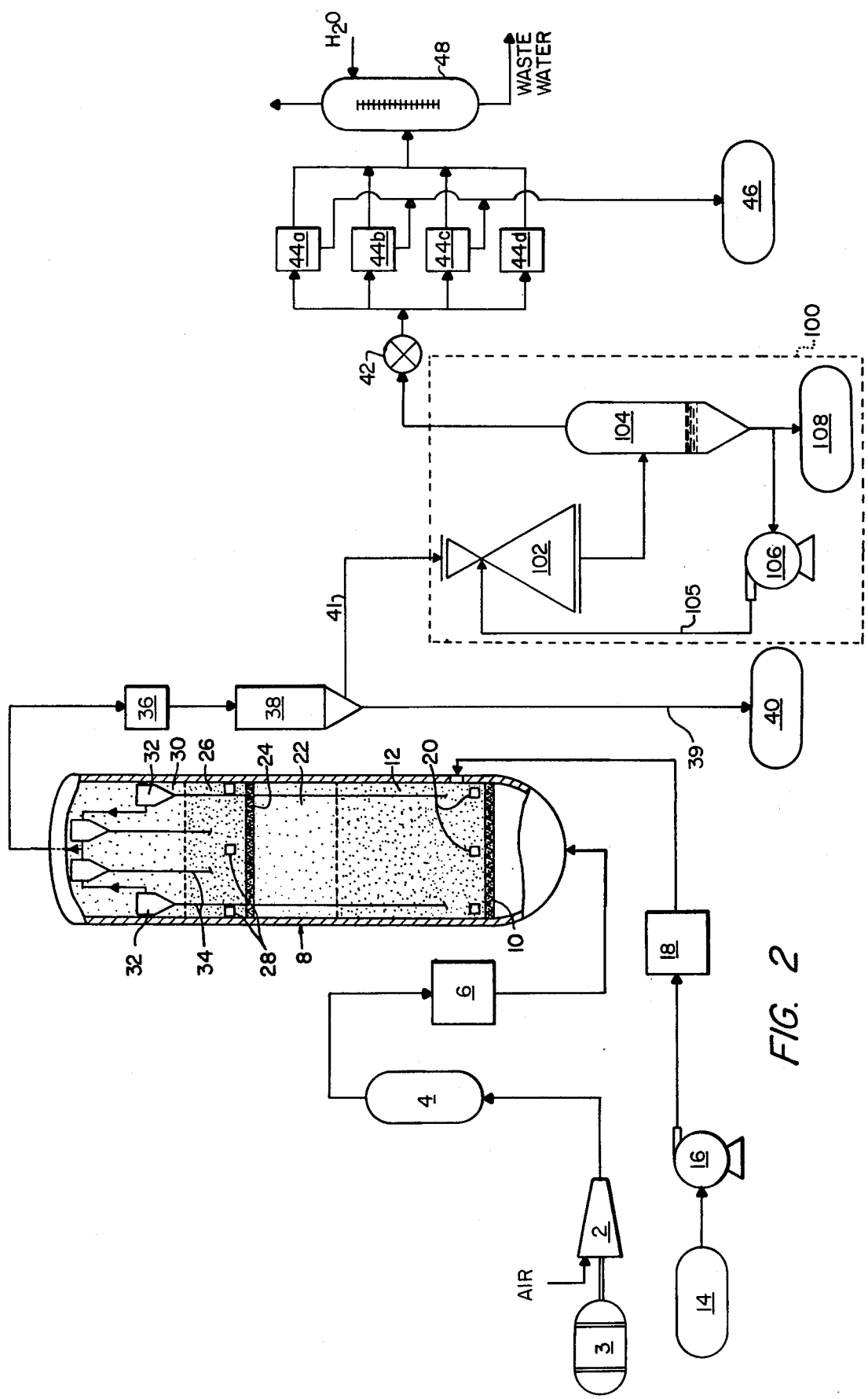
FIG. 2 is a process flow sheet showing a system constituting the preferred form of the invention for producing phthalic anhydride by catalytic oxidation of naphthalene.

The system shown in FIG. 2 is identical to the system shown in FIG. 1, except that a venturi scrubber stage 100 has been inserted into the system in the effluent line 41 between partial condenser 38 and pressure control valve 42. This venturi scrubber stage 100 functions to remove substantially all of the catalyst dust in the effluent stream before the effluent reaches the switch condensers, without increasing significantly back pressure in the system. To emphasize that the system of FIG. 2 is identical to the system of FIG. 1 except for the addition of venturi scrubber stage 100, the components common to the two systems have been represented in FIG. 2 with the same symbols and given the same reference numerals as they were in FIG. 1.

The Venturi scrubber stage comprises a venturi 102, a separator vessel 104, a recycle pump 106, and a storage tank 108. Pump 106 is disposed in a line 105 connecting a drawoff port of separator 104 to venturi 102. The drawoff port of vessel 104 is also connected to tank 108, while the overhead port of vessel 104 is connected to the switch condensers via pressure control valve 42.

Since the preferred operating conditions of the new system shown in FIG. 2 are the same as those for the system shown in FIG. 1 up to the point where the effluent stream leaves partial condenser 38, a description of the operation of that portion of the new system will be omitted here for the sake of convenience and the following description will explain the operation of the remainder of the system, i.e., what happens in the system after the effluent leaves condenser 38.

As the effluent stream leaves partial condenser 38, at a temperature of approximately 300° F., it is routed through venturi scrubber stage 100 to effect removal of substantially all the catalyst particles entrained in the effluent. In scrubber stage 100 the effluent stream is passed into the entrance of a venturi 102, where it comes into contact with a scrubbing stream of molten phthalic anhydride which is injected into the throat of venturi 102 via line 105. This contact knocks the catalyst particles in the effluent out of the effluent and into the molten phthalic anhydride where it is captivated. Thereafter, the molten phthalic anhydride (bearing the catalyst particles) and the reactor effluent (devoid of catalyst particles) are passed to a separator 104 where the molten phthalic anhydride is recycled by a pump 106 for reinjection into the throat of venturi 102, and the gaseous effluent is sent off to pressure control valve 42 and the battery of switch condensers 44. The catalyst dust which exited partial condenser 38 and entered venturi 102 within the reactor effluent, however, is entrapped in the phthalic anhydride circulating in the scrubber system, and the effluent leaving separator 104 and heading for pressure control valve 42 is substantially dust free. As a result, when the effluent reaches switch condensers 44 the phthalic anhydride in the effluent can be easily recovered via direct sublimation to a solid without the troublesome formation of phthalic anhydride sludge within the switch condensers.

In order to prevent the level of catalyst particles in the cycling phthalic anhydride from building up to the point where it might interfere with the scrubbing operation, part of the cycling phthalic anhydride is continually purged away to tank 108. This purged phthalic anhydride can then be refined to remove the captured catalyst particles and the cleansed phthalic anhydride can then be combined with molten phthalic anhydride accumulated in storage tank 46.

The molten phthalic anhydride recirculated in line 105 of the scrubbing apparatus is kept at about 290° F. so that its temperature is very near to that of the effluent entering the venturi. This close temperature proximity between the scrubbing liquid and the effluent is desired to ensure that there is no rapid shock cooling of the effluent at the venturi which might inhibit the efficiency of the scrubbing operation.

EXAMPLE

A reactor as generally illustrated in FIG. 2 of the drawings, having a diameter of approximately 10 feet and a height of about 100 feet, is charged with about 65,000 pounds of a vanadium pentoxide-containing catalyst in its bed 12, and with about 35,000 pounds of the same catalyst in its bed 26. Air is fed into the bottom of the reactor at about 5790 standard cubic feet per minute, at a pressure of about 37 psig and a temperature of about 300° F. Naphthalene is metered into the catalyst bed 12 at a rate of about 135 standard cubic feed per minute, at a pressure of about 35 psig and a temperture of about 500° F. The air to naphthalene ratio entering the fluidized bed 12 is about 10:1 by weight. The gaseous mixture of air, naphthalene and reaction products pass upwardly at a superficial velocity of about 1 to 1.5 feet per second, fluidizing the catalyst particles in bed 12 so that the bed has a height of about 25 feet. The average pressure in the fluidized bed is about 30 pounds per square inch gauge. The reaction temperature of fluidized bed 12 is maintained at about 675° F., which is the temperature which produces the maximum yield of phthalic anhydride.

The gases passing out of bed 12 pass through the disengagement zone 22, approximately 35 feet in height, and then encounter and fluidize the catalyst bed 26. Bed 26 is fluidized to a height of approximately 15 feet by the rising gases. The gases in bed 26 are quenched at a temperature of approximately 525° F. and then they pass on to a disengagement zone 30 approximately 25 feet in height.

Next the gases are passed through cyclones 32 for removal of catalyst particles. The gas stream leaves cyclones 32 at a temperature of about 500° F. and passes to a gas cooler 36 where the stream is cooled to a temperature of about 315° F. Then the stream is passed to a partial condenser 38 where about ½ of the phthalic anhydride is liquified and removed from the gases and recovered in tank 40.

The gas stream leaving condenser 38 enters venturi 102 at a temperature of about 300° F. and a pressure of about 18 psig, and meets a stream of molten phthalic anhydride which is injected into the throat of the venturi at a temperature of about 290° F. and a pressure of about 17 psig. The molten phthalic anhydride scrubs the catalyst particles from the effluent. The dust-laden molten phthalic anhydride and the gas stream are separated in separator 104, with the gases passing to the switch condensers 44a, 44b, 44c, etc., and the molten phthalic anhydride passing partly to drawoff tank 108 and partly through recycle line 105 back to venturi 102. About 80 to 90% of the phthalic anhydride removed from separator 104 is recycled to venturi 102. The gas stream is directed into selected ones of the switch condensers for sublimation depositions. The gas stream enters the selected switch condener(s) at a pressure of about 3-4 psig and a temperature of about 290° F. The switch condensers are operated so as to sublimate out phthalic anhydride at a rate of about 99.5% of that entering them. The gases exiting the switch condensers have a temperature of about 125° F.

The concentrations of catalyst dust in the gaseous effluent entering venturi 102 is about 0.01% by weight. As a consequense of the dust removal effected by scrubber stage 100, the catalyst concentration in the effluent entering the switch condensers is reduced to less than 10 ppm. Because of the reduction in catalyst dust concentration, the system is able to recover over 99.5% of all the phthalic anhydride produced in fluidized catalytic reactor 8.

MODIFICATIONS OF THE PREFERRED EMBODIMENT

It is, of course, possible to modify the phthalic anhydride production system shown in FIG. 2 without departing from the scope of the present invention.

Thus, for example, the invention may be practiced with a fluid bed reactor having a single fluid bed or a plurality of fluid beds. Alternatively, the invention may be practiced with a fixed bed reactor.

It also is to be understood that the invention may be practiced with different operating conditions, e.g., the air may enter the reaction vessel at ambient temperature and undergo all heating within the reactor itself, or the naphthalene may be fed into the reactor as a liquid and be vaporized upon contact with catalyst bed 12.

The system also may be modified in obvious ways. For example, the number of switch condensers may be varied.

It is also contemplated that one may omit gas cooler 36 from the system and pass the reactor effluent directly from the reactor to partial condenser 38.

The system shown in FIG. 2 also may be adapted to produce phthalic anhydride by the oxidation of ortho-xylene. In such a case, it might be necessary to use special promoters (as described in U.S. Pat. No. 3,407,215) or a special catalyst (as described in British Pat. No. 1,192,416) to support the reaction within the reactor.

The present invention also may be used to prepare anhydrides of carboxylic and dicarboxylic acids other than phthalic anhydride by the catalytic oxidation of aromatic hydrocarbons such as benzene, ortho-xylene or naphthalene, or of unsaturated aliphatic hydrocarbons such as butadiene, n-butene or mixtures containing butadiene and/or n-butene.

These and other changes in their type are well known to those skilled in the art and considered within the scope of the present invention.

ADVANTAGES OF THE INVENTION

Several advantages are obtained by using the present invention.

First, by employing the phthalic anhydride production system shown in FIG. 2 instead of the phthalic anhydride production system shown in FIG. 1, it is possible to remove substantially all of the catalyst dust from the reactor effluent before the effluent enters the switch condensers. As a consequence, phthalic anhydride is recovered in the switch condensers as sublimated needle-like crystals (relatively porous and having a relatively good heat transfer coefficient) instead of being recovered as a dense slushy mass (relatively unporous and having a relatively poor heat transfer coefficient). As a result the production system shown in FIG. 2 operates more efficiently and economically than the production system shown in FIG. 1, since the level of back pressure in the switch condensers is reduced, and also because the switch condensers can separate out and recover greater quantities of phthalic anhydride for a given level of heat exchanger work.

Second by employing the phthalic anhydride production system shown in FIG. 2 instead of modifying, as suggested previously, the phthalic anhydride production system of FIG. 1 to replace the cyclones with a more effective type of filtration system (i.e., screens, micro-metallic fibers, or fiber filters), it is possible to obtain the same dust-free effluent without the increases in system back pressure which accompany the use of screens or filters. As a result, the production system shown in FIG. 2 operates more efficiently and economically than the modified version of the production system of FIG. 1 which substitutes screens or filters for the cyclones.

Another advantage of the present invention is that conventional production systems of the type shown in FIG. 1 can be modified easily and relatively economically to incorporate the present invention.

In addition, the present invention may be practiced in systems for producing products other than phthalic anhydride, i.e., it can be utilized in systems producing anhydrides of carboxylic and dicarboxylic acid by the catalytic oxidation of aromatic hydrocarbons such as benzene, ortho-xylene or naphthalene, or of unsaturated aliphatic hydrocarbons such as butadiene, n-butene, or mixtures of butadiene and/or n-butene.

Still other advantages will be obvious to persons skilled in the art.

What I claim is:

1. A process for producing an acid anhydride, said process comprising the steps of:
   (a) reacting an aromatic hydrocarbon or an unsaturated aliphatic hydrocarbon with oxygen in a reactor in the presence of a catalyst so as to produce a gas stream which comprises an anhydride of a carboxylic or discarboxylic acid;
   (b) passing said gas stream from said reactor to a partial condenser where a portion of said anhydride is condensed out of said gas stream as a liquid and is recovered;
   (c) passing said gas stream from said partial condenser to a venturi scrubber stage and scrubbing said gas stream so as to purge it of substantially all entrained catalyst dust particles;
   (d) passing said gas stream from said scrubber stage to at least one switch condenser;
   (e) sublimating substantially all of said anhydride remaining in said gas stream so as to form a solid in said at least one condenser; and
   (f) recovering said solid from said at least one condenser.

2. A process according to claim 1 wherein said venturi scrubber stage comprises a venturi and a separator, and further wherein said gas stream passes from said condenser into said venturi in contact with recycled liquid anhydride and the mixture of said gas stream and liquid anhydride is passed from said venturi into said separator where said liquid anhydride and said entrained dust particles are separated from said gas stream, whereby said gas stream is substantially free of dust particles as it passes to said at least one switch condenser.

3. A process according to claim 2 wherein at least some of the liquid anhydride separated from said gas stream in said separator is purged.

4. A process according to claim 2 wherein at least some of the anhydride separated from said gas stream is recycled to said scrubber and the remainder of said liquid anhydride is recovered from the scrubber stage so as to limit the buildup of catalyst dust particles in the liquid anhydride recycled to the venturi.

5. A process according to claim 4 wherein said liquid anhydride circulating in said scrubber stage is maintained at a temperature close to the temperature of said gas stream as it enters said scrubber stage, in order that said gas stream will not undergo rapid shock cooling when it is contacted with said liquid anhydride in said scrubber stage.

6. A process according to claim 1 wherein said reactants comprise oxygen and naphthalene, and further wherein said catalyst comprises vanadium pentoxide.

7. A process according to claim 6 wherein said catalyst is fluidized in said reactor.

8. A process according to claim 1 further including the step of cooling said gas stream after it leaves said reactor and before it arrives at said partial condenser.

9. A process according to claim 1 wherein said gas stream flows through a pressure control valve after it leaves said scrubber stage and before it reaches said at least one switch condenser, and further wherein said pressure control valve maintains a back pressure of about 22 psig.

10. A process for producing phthalic anhydride, said process comprising the steps of:
(a) reacting naphthalene or xylene with oxygen in a reactor in the presence of a catalyst under selected conditions so as to produce a gas stream which comprises phthalic anhydride;
(b) passing said gas stream from said reactor to a partial condenser where a portion of said phthalic anhydride is condensed out of said gas stream as a liquid and is recovered;
(c) passing said gas stream from said partial condenser to a venturi scrubber stage and scrubbing said gas stream so as to purge it of substantially of entrained catalyst dust particles;
(d) passing said gas stream from said scrubber stage to at least one switch condenser;
(e) causing substantially all of said phthalic anhydride remaining in said gas stream to form a solid in said at least on condenser; and
(f) recovering said solid from said at least one condenser.

11. A process according to claim 10 wherein said venturi scrubber stage comprises a venturi and a separator, and further wherein said gas stream passes from said condenser into said venturi in contact with recycled liquid phthalic anhydride and the mixture of said gas stream and liquid phthalic anhydride is passed from said venturi into said separator where said liquid phthalic anhydride and said entrained dust particles are separated from said gas stream, whereby said gas stream is substantially free of dust particles as it passes to said at least one switch condenser.

12. A process according to claim 11 wherein at least some of the liquid phthalic anhydride separated from said gas stream in said separator is purged.

13. A process according to claim 11 wherein at least some of the phthalic anhydride separated from said gas stream is recycled to said scrubber and the remainder of said liquid phthalic anhydride is recovered from the scrubber stage so as to limit the buildup of catalyst dust particles in the liquid phthalic anhydride recycled to the venturi.

14. A process according to claim 4 wherein said liquid phthalic anhydride circulating in said scrubber stage is maintained at a temperature close to the temperature of said gas stream as it enters said scrubber stage, in order that said gas stream will not undergo rapid shock cooling when it is contacted with said liquid phthalic anhydride in said scrubber stage.

15. A process according to claim 10 wherein said gas stream enters said venturi scrubber stage at a temperature of about 300° F., and said liquid phthalic anhydride is heated to a temperature of about 290° F.

16. A process according to claim 10 wherein said catalyst comprises vanadium pentoxide.

17. A process according to claim 10 wherein said catalyst is fluidized in said reactor.

18. A process according to claim 10 further including the step of cooling said gas stream after it leaves said reactor and before it arrives at said partial condenser.

19. A process according to claim 18 wherein said gas stream exits from said reactor at a temperature of about 525° F., and said gas stream is cooled to a temperature of about 315° F. before it enters said partial condenser.

20. A process according to claim 18 wherein said gas stream flows through a pressure control valve after it leaves said scrubber stage and before it reaches said at least one switch condenser, and further wherein said pressure control valve maintains a back pressure of about 22 psig.

* * * * *

UNITED STATES PATENT AND TRADEMARK OFFICE
CERTIFICATE OF CORRECTION

PATENT NO. : 4435580
DATED : March 6, 1984
INVENTOR(S) : Constantine D. Miserlis It is certified that error appears in the above-identified patent and that said Letters Patent is hereby corrected as shown below:

Claim 10, column 9, line 32, the word "of" (second occurrence) should be -- all --.

Claim 10, column 9, line 38, the word "on" should be -- one --.

Signed and Sealed this

Twelfth Day of June 1984

[SEAL]

*Attest:*

*Attesting Officer*

GERALD J. MOSSINGHOFF

*Commissioner of Patents and Trademarks*